(12) United States Patent
Vandewalle

(10) Patent No.: US 8,322,256 B2
(45) Date of Patent: *Dec. 4, 2012

(54) SYSTEM FOR FORMING A TENDON-BONE GRAFT

(75) Inventor: Mark V. Vandewalle, Pierceton, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 655 days.

This patent is subject to a terminal disclaimer.

(21) Appl. No.: 12/436,361

(22) Filed: May 6, 2009

(65) Prior Publication Data

US 2009/0222052 A1 Sep. 3, 2009

Related U.S. Application Data

(63) Continuation-in-part of application No. 11/867,928, filed on Oct. 5, 2007.

(51) Int. Cl.
*B23B 3/26* (2006.01)
*B23B 3/00* (2006.01)
(52) U.S. Cl. ............................. 82/101; 82/110
(58) Field of Classification Search .......... 606/79, 606/86; 82/117, 101, 110; 29/27 C, 560
See application file for complete search history.

(56) References Cited

U.S. PATENT DOCUMENTS

| | | | |
|---|---|---|---|
| 43,909 A | 8/1864 | Hair | |
| 493,730 A | 3/1893 | MacKenzie | |
| 1,911,873 A | 5/1933 | Balton | |
| 2,573,462 A | 10/1951 | Lindsey | |
| 2,591,516 A | 4/1952 | Darnell | |
| 3,835,849 A | 9/1974 | McGuire | |
| 3,848,601 A | 11/1974 | Ma et al. | |
| 4,007,732 A | 2/1977 | Kvavle et al. | |
| 4,010,737 A | 3/1977 | Vilaghy et al. | |
| 4,059,115 A | 11/1977 | Jumashev et al. | |
| 4,177,797 A | 12/1979 | Baylis et al. | |
| 4,416,278 A | 11/1983 | Miller | |

(Continued)

FOREIGN PATENT DOCUMENTS

DE 19503504 A1 3/1996

(Continued)

OTHER PUBLICATIONS

"Matrices for Cartilage Repair," Coutes, et al., published in Clinical Orthopaedics & Related Research, No. 391S pp. S271-S279, copyright 2001 Lippincott Williams & Wilkins, Inc.

(Continued)

*Primary Examiner* — Will Fridie, Jr.
(74) *Attorney, Agent, or Firm* — Harness, Dickey

(57) ABSTRACT

A system for forming a tendon-bone graft. The system can include a support member that is adapted to support the tendon-bone graft. The system can further include a first clamp that is adapted to engage the support member and the tendon-bone graft to orient and hold the tendon-bone graft on the support member in a first direction, and a second clamp that is adapted to engage the tendon-bone graft to clamp the tendon-bone graft to the support member in a second direction. The system can also include a shaping member that is operable to resect the tendon-bone graft. The shaping member can be moveable relative to at least one of the first clamp and the second clamp to resect the tendon-bone graft.

24 Claims, 8 Drawing Sheets

U.S. PATENT DOCUMENTS

| | | | |
|---|---|---|---|
| 4,565,192 A | 1/1986 | Shapiro | |
| 4,627,853 A | 12/1986 | Campbell et al. | |
| 4,649,918 A | 3/1987 | Pegg et al. | |
| 4,741,651 A | 5/1988 | Despres | |
| 4,782,833 A | 11/1988 | Einhorn et al. | |
| 4,904,259 A | 2/1990 | Itay | |
| 4,913,143 A | 4/1990 | Oloff et al. | |
| 4,936,313 A | 6/1990 | Burkhardt et al. | |
| 5,041,117 A | 8/1991 | Engelhardt | |
| 5,053,050 A | 10/1991 | Itay | |
| 5,139,520 A | 8/1992 | Rosenberg | |
| 5,152,763 A | 10/1992 | Johnson | |
| 5,197,967 A | 3/1993 | Wilson | |
| 5,211,647 A | 5/1993 | Schmieding | |
| 5,269,786 A | 12/1993 | Morgan | |
| 5,320,115 A | 6/1994 | Kenna | |
| 5,320,626 A | 6/1994 | Schmieding | |
| 5,341,816 A | 8/1994 | Allen | |
| 5,397,357 A | 3/1995 | Schmieding et al. | |
| 5,415,651 A | 5/1995 | Schmieding | |
| 5,423,823 A | 6/1995 | Schmieding | |
| 5,496,326 A | 3/1996 | Johnson | |
| 5,513,662 A | 5/1996 | Morse et al. | |
| 5,540,692 A * | 7/1996 | Tidwell | 606/79 |
| 5,562,669 A | 10/1996 | McGuire | |
| 5,603,716 A | 2/1997 | Morgan et al. | |
| 5,655,546 A | 8/1997 | Halpern | |
| 5,733,289 A | 3/1998 | Seedhom et al. | |
| 5,782,835 A | 7/1998 | Hart et al. | |
| 5,785,714 A | 7/1998 | Morgan et al. | |
| 5,817,098 A | 10/1998 | Albrektsson et al. | |
| 5,827,288 A | 10/1998 | Umber et al. | |
| 5,865,834 A | 2/1999 | McGuire | |
| 5,885,293 A | 3/1999 | McDevitt | |
| 5,895,390 A | 4/1999 | Moran et al. | |
| 5,904,717 A | 5/1999 | Brekke et al. | |
| 5,918,604 A | 7/1999 | Whelan | |
| 5,919,196 A | 7/1999 | Bobic et al. | |
| 6,007,496 A | 12/1999 | Brannon | |
| 6,017,348 A | 1/2000 | Hart et al. | |
| 6,110,178 A | 8/2000 | Zech et al. | |
| 6,146,385 A | 11/2000 | Torrie et al. | |
| 6,179,839 B1 | 1/2001 | Weiss et al. | |
| 6,179,871 B1 | 1/2001 | Halpern | |
| 6,187,329 B1 | 2/2001 | Agrawal et al. | |
| 6,231,577 B1 * | 5/2001 | Canedy | 606/79 |
| 6,242,247 B1 | 6/2001 | Rieser et al. | |
| 6,280,447 B1 | 8/2001 | Marino et al. | |
| 6,358,253 B1 | 3/2002 | Torrie et al. | |
| 6,375,658 B1 | 4/2002 | Hangody et al. | |
| 6,387,693 B2 | 5/2002 | Rieser et al. | |
| 6,395,011 B1 | 5/2002 | Johanson et al. | |
| 6,442,814 B1 * | 9/2002 | Landry et al. | 29/26 B |
| 6,458,144 B1 * | 10/2002 | Morris et al. | 606/179 |
| 6,488,033 B1 | 12/2002 | Cerundolo | |
| 6,528,052 B1 | 3/2003 | Smith et al. | |
| 6,530,928 B1 | 3/2003 | Frei et al. | |
| 6,557,226 B1 * | 5/2003 | Landry et al. | 29/27 C |
| 6,591,581 B2 | 7/2003 | Schmieding | |
| 6,592,588 B1 | 7/2003 | Bobic et al. | |
| 6,607,534 B2 | 8/2003 | Bonutti | |
| 6,613,054 B2 | 9/2003 | Scribner et al. | |
| 6,685,709 B2 | 2/2004 | Sklar | |
| 6,696,073 B2 | 2/2004 | Boyce et al. | |
| 6,727,224 B1 | 4/2004 | Zhang et al. | |
| 6,740,484 B1 | 5/2004 | Khirabadii et al. | |
| 6,796,977 B2 | 9/2004 | Yap et al. | |
| 6,835,377 B2 | 12/2004 | Goldberg et al. | |
| 6,852,114 B2 | 2/2005 | Cerundolo | |
| 6,962,592 B2 * | 11/2005 | Gatturna et al. | 606/79 |
| 7,231,815 B2 | 6/2007 | Kanare | |
| 7,241,316 B2 | 7/2007 | Evans et al. | |
| 7,347,130 B2 * | 3/2008 | Pham et al. | 82/101 |
| 2001/0027322 A1 | 10/2001 | Bowman | |
| 2001/0039455 A1 | 11/2001 | Simon et al. | |
| 2002/0022847 A1 | 2/2002 | Ray, III et al. | |
| 2002/0082704 A1 | 6/2002 | Cerundolo | |
| 2002/0095214 A1 | 7/2002 | Hyde, Jr. | |
| 2003/0009218 A1 | 1/2003 | Boucher et al. | |
| 2003/0130662 A1 | 7/2003 | Michelson | |
| 2003/0212435 A1 | 11/2003 | Gold et al. | |
| 2004/0106928 A1 | 6/2004 | Ek | |
| 2004/0162622 A1 | 8/2004 | Simon et al. | |
| 2004/0210227 A1 | 10/2004 | Trail et al. | |
| 2004/0230303 A1 | 11/2004 | Gomes et al. | |
| 2005/0064042 A1 | 3/2005 | Vunjak-Novakovic et al. | |
| 2005/0222576 A1 | 10/2005 | Kick et al. | |
| 2006/0142775 A1 | 6/2006 | Heneberry et al. | |
| 2007/0093896 A1 | 4/2007 | Malinin | |
| 2007/0135917 A1 | 6/2007 | Malinin | |
| 2007/0135918 A1 | 6/2007 | Malinin | |
| 2007/0135928 A1 | 6/2007 | Malinin | |
| 2007/0276506 A1 | 11/2007 | Troxel | |
| 2009/0093853 A1 | 4/2009 | Missos et al. | |

FOREIGN PATENT DOCUMENTS

| | | |
|---|---|---|
| WO | WO-9106246 | 5/1991 |
| WO | WO-2004103224 | 12/2004 |

OTHER PUBLICATIONS

"Techniques for ACL Reconstruction with Multi-Trac™ Drill Guide," available by 2000.

Acufex Microsurgical, Inc., "Endoscopic Technique for ACL Reconstruction with Pro-Trac Tibial Guide: Endobutton Fixation," available by 2000.

Arthrex, "Osteochondral Autograft Transfer System (OATS), Key Words: Chondral defects, osteochondral cylinder transplants, arthroscopic technique, chronic ACL deficiency" © Arthrex Inc.,1996 (1 page).

Arthrex, Osteochondral Autograft Transfer System (OATS), "Surgical Technique," [undated] (pp. 1-21).

Arthrex, Osteochondral Autograft Transfer System (OATS)™, "Surgical Technique," 1996 (pp. 1-24).

Arthrotek® OCD System, Osteochondral Defect Surgical Technique, brochure, © 1999 (4 pages).

Christel, P., et al., "Osteochondral Grafting Using Mosaicplasty Technique," www.maitrise-orthop.com/corpusmaitri/orthopaedic/mo76_mosaicplasty/index.shtml (23 pages).

Chu et al., Articular Cartilage Transplantation—Clinical Results in the Knee, clinical Orthopaedics and Related Research, No. 360, pp. 159-168 Lippincott, Williams 8 Wilkins, (Mar. 1999).

Convery et al., "Long-Term Survival of Chondrocytes in an Osteochondral Articular Cartilage Allograft," Journal of Bone and Joint Surgery, vol. 78-A, No. 7, pp. 1082-1088 (Jul. 1996).

Gross, M.D., Allan, "Cartilage Resurfacing Filling Defects," The Journal of Arthroplasty vol. 18 No. 3 Suppl. 1 (2003) pp. 14-17.

Hangody et al., Autologous Osteochondral Mosaicplasty for the Treatment of Full-Thickness Defects of Weight-Bearing Joints, Journal of Bone and Joint Surgery, vol. 85-a, Supp. 2, pp. 25-32 (2003).

Hangody, et al., "Arthroscopic autogenous osteochondral mosaicplasty for the treatment of femoral condylar articular defects, A preliminary report," Knee, Surg, Sports Traumatol, Arthrosc (1997) © Springer-Verlag 1997 5:262-267.

Hangody, M.D., et al., "MosaicPlasty™ Osteochondral Grafting Technique Guide", Smith & Nephew Endoscopy, © 1996.

Innovasive Cor™ System, © 1997 Innovasive Devices, Inc. (2 pages).

Instrument Makar, Inc., "Bone Grafters Surgical Technique," Dec. 1995.

Instrument Makar, Inc.,"New Directions in Arthroscopic Innovation," 1991 Catalogue.

Jakob, M.D., Roland, et al., "Autologous Osteochondral grafting in the Knee: Indication, Results, and Reflections," Clinical Orthopaedics and Related Research No. 401, (2002) pp. 170-184.

Levitt, M.D., et al., Articular Cartilage Resurfacing with Fresh Pre-Cut Osteochondral Core Allografts, Power Point Presentation, University of Miami, Department of Orthopaedics and Rehabilitation [undated].

Malinin, T., M.D., Human Cadaver Femoral Head Homografts for Anterior Cervical Spine Fusions, Reprinted from Surgical Neurology, vol. 7, No. 4, apr. 1977, Copyright, © 1977.

Malinin, T.I., "University of Miami Tissue Bank: Collection of Postmortem Tissues for Clinical Use and Laboratory Investigation", From the Departments of Surgery and Pathology, University of Miami School of Medicine and the Veterans Administration Hospital, Transplantation Proceedings, vol. VIII, No. 2, Supplement 1 (June), 1976 (pp. 53-58).

Malinin et al., "Articular Cartilage Nutrition is Mediated by Subchondral Bone: a Long-Term Autograft Study in Baboons," Osteoarthritis and Cartilage, vol. 8, pp. 483-491, OsteoArthritis Research Society Intl. (2000).

Malinin et al., Hypothermic Storage and Cryopreservation of Cartilage, Clinical Orthopedics and Related Research, No. 197, pp. 1526 (Jul.-Aug. 1985).

Matsusue, Y., et al., "Arthroplasty using Mosaicplasty,", NCBI Pub Med, www.ncbi.nlm.nih.gov/entrez/query.fcgi?CMD=Display&DB=pubmed [printed May 29, 2007].

Szerb, M.D., et al., "Mosaicplasty, Long-Term Follow-Up," Bulletin of the Hospital for Joint Diseases, vol. 63, Nos. 1 & 2 (2005), pp. 54-62.

Williams et al.. "Prolonged Storage Effects on the Articular Cartilage of Fresh Human Osteochondral Allografts," Journal of Bone and Joint Surgery, vol. 85-A, No. 1 1, pp. 21 11-21 20 (Nov. 2003).

* cited by examiner

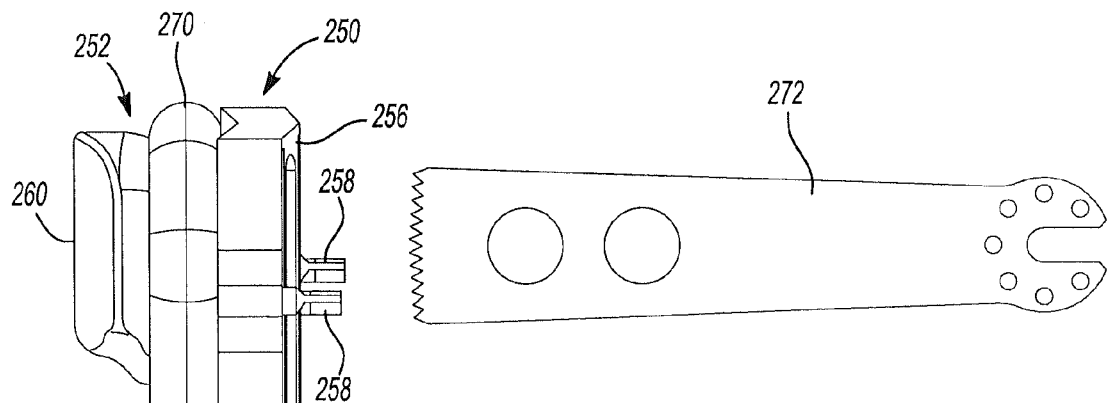
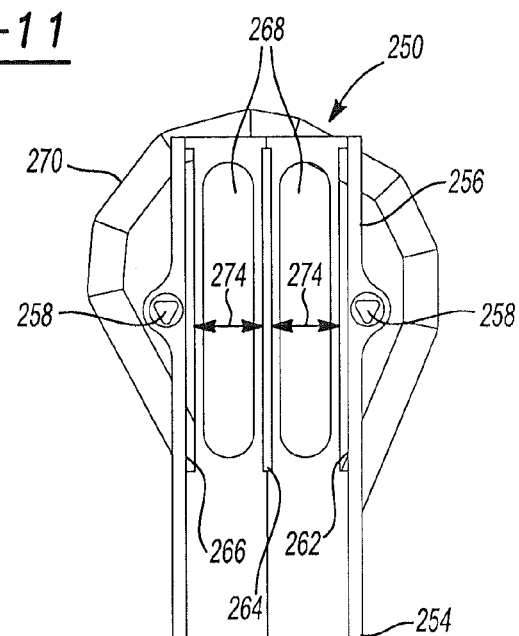

SYSTEM FOR FORMING A TENDON-BONE GRAFT

CROSS-REFERENCE TO RELATED APPLICATIONS

This application is a continuation-in-part of U.S. patent application Ser. No. 11/867,928 filed on Oct. 5, 2007, and published on Apr. 9, 2009 as U.S. Application Publication No. 2009/0093853, which is incorporated herein by reference.

FIELD

The present disclosure relates generally to ligament reconstruction surgery, and more specifically, to systems and methods for forming a tendon-bone graft.

BACKGROUND

The statements in this section merely provide background information related to the present disclosure and may not constitute prior art.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. During these procedures, surgeons can use orthopedic implants to restore function to the site and facilitate the natural healing process.

Current orthopedic implants are generally composed of non-resorbable metals, ceramics, polymers, and composites. However, in some instances, it may be desirable to have an implant made from donor tissues. For example, in the case of an anterior cruciate ligament (ACL) reconstruction, surgeons can implant a tendon-bone graft. The tendon-bone graft can be recovered from the Achilles tendon/calcaneus or from the patella/patellar ligament/tibia portions of donor tissue. Prior to implantation, the donor bone may be formed into a cylindrical shape so that it can be inserted into a drilled tunnel in the anatomy. Typically, the surgeon carves the bone block into the cylindrical shape, as the presence of the ligament on one side of the bone block makes clamping and conventional cutting techniques impractical.

SUMMARY

This section provides a general summary of the disclosure, and is not a comprehensive disclosure of its full scope or all of its features.

In one form, a system for forming a bone graft, such as a tendon-bone graft, is provided. The system can include a support member that is adapted to support the tendon-bone graft. The system can further include a first clamp that is adapted to engage the support member and the tendon-bone graft to orient and hold the tendon-bone graft on the support member in a first direction, and a second clamp that is adapted to engage the tendon-bone graft to clamp the tendon-bone graft to the support member in a second direction. The system can also include a shaping member that is operable to resect the tendon-bone graft. The shaping member can be moveable relative to at least one of the first clamp and the second clamp to resect the tendon-bone graft.

In another form, a method for forming a tendon-bone graft is provided. The method can include placing a tendon-bone graft on a support and applying a first clamping force in a first direction against the tendon-bone graft to orient and hold the tendon-bone graft on the support. A second clamping force can be applied in a second direction different than the first direction to clamp the tendon-bone graft on the support. The method can also include moving a shaping member substantially perpendicular to the first and second clamping forces to resect a first portion of the tendon-bone graft. The method can further include positioning the shaping member over the first resected portion of the tendon-bone graft and securing the shaping member to a first clamp. A second portion of the tendon-bone graft can then be resected using the secured shaping member as a guide for the resection of the second portion.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 11 is a side view of a guide of the system for forming a tendon-bone graft according to the principles of the present disclosure; and FIG. 12 is a front view of the guide of FIG. 11 according to the principles of the present disclosure.

DETAILED DESCRIPTION

Figure 1:
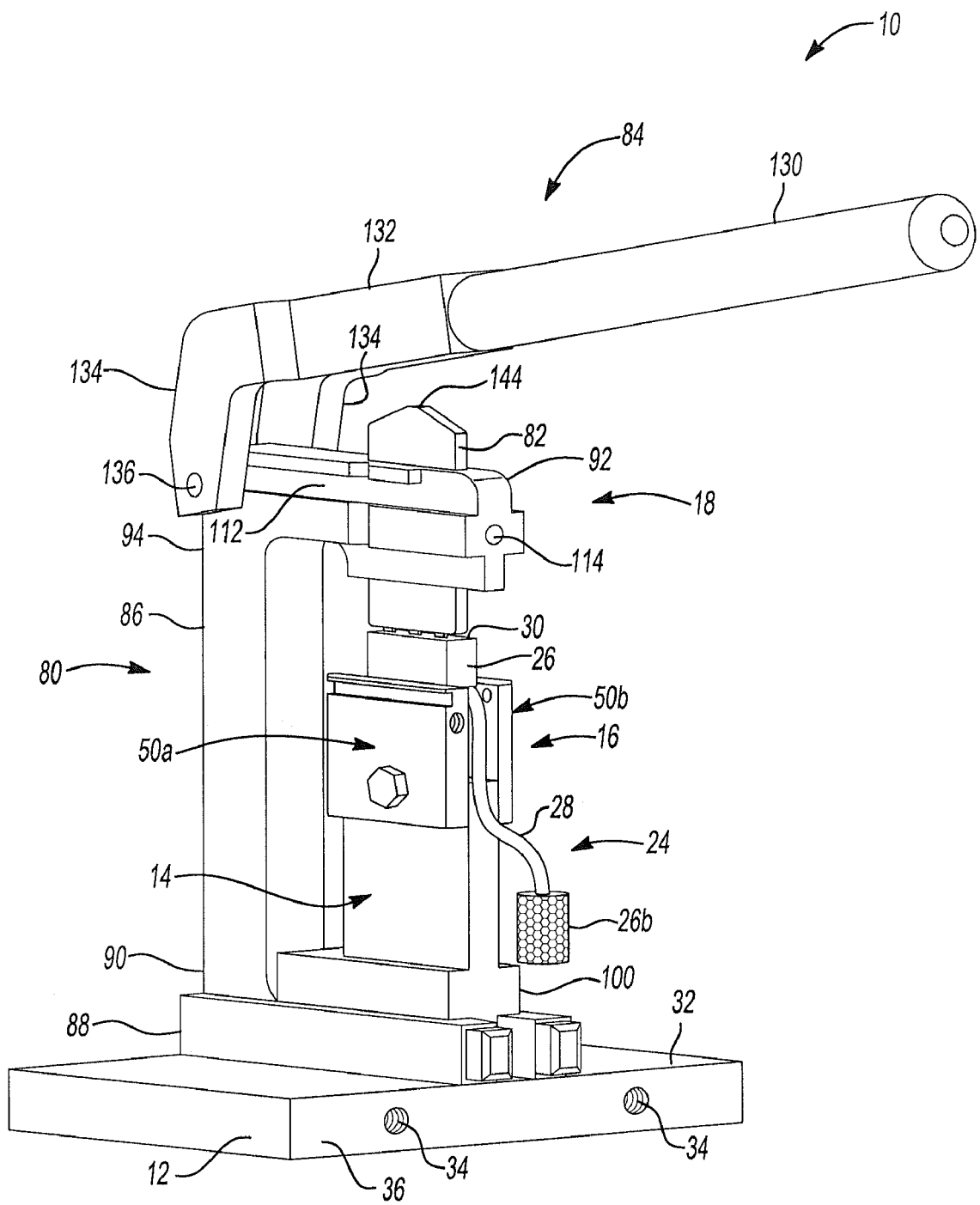
FIG. 1 is a perspective schematic view of a system for forming a tendon-bone graft according to the principles of the present disclosure.

The following description is merely exemplary in nature and is not intended to limit the present disclosure, application, or uses. It should be understood that throughout the drawings, corresponding reference numerals indicate like or corresponding parts and features. Although the following description can be related generally to a tendon-bone graft forming system that can be used to sculpt or resect a tendon-bone graft prior to positioning the tendon-bone graft in a prepared portion of the anatomy, such as in a femur and a tibia, it will be understood that the tendon-bone graft forming system, as described and claimed herein, can be used to sculpt or resect any appropriate graft for any appropriate use. For example, a bone-tendon-bone graft or only a bone graft can also be formed as described herein. Therefore, it will be understood that the following discussions are not intended to limit the scope of the appended claims.

With reference to FIGS. 1-6, a graft forming system 10 is shown. The graft forming system 10 can include a base 12, at least one support 14, a first clamping system 16, a second clamping system 18, and a shaping member 20. The system 10 can be composed of any suitable sterilizable material, such as a metal or metal alloy including, but not limited to, stainless steel. The system 10 can enable a user to form a tendon-bone graft 24 including at least one bone block 26 and a tendon 28. Alternatively, a bone-tendon-bone graft or a bone block can also be formed. The system 10 can be used to form the bone block 26 into a desired shape, such as a cylindrical or substantially cylindrical shape 26b, prior to insertion of the tendon-bone graft into an anatomy.

The base 12 can include any suitable member or surface to which the support 14 and the second clamping system 18 can be coupled. Base 12 can include a rectangular shape having a surface 32 and two threaded bores 34 positioned on a side face 36 of base 12 for optionally receiving stabilizing rods 38. Support 14 and second clamping system 18 can be operatively coupled to surface 32 of base 12. The stabilizing rods 38 can be used to provide increased stability of forming system 10 when base 12 is operated in a state where base 12 is not secured to another structure. By using stabilizing rods 38 for additional stability, base 12 can have a smaller footprint thereby being lighter and easier to transport. While base 12 is shown as having a rectangular shape and receiving stabilizing rods 38, it should be appreciated that base 12 and/or stabilizing rods 38 can be optional, and the support 14 and second clamping system 18 can be operatively coupled to another structure such as an operating table or a tray in an operating room or other facility.

The support 14 can include a distal end 42 and a proximal end 44 and can be formed of any suitable sterilizable material, such as a metal or metal alloy. The distal end 42 can be coupled to base 12 in any suitable manner, such as by fasteners, and the proximal end 44 can support the bone block 26. The proximal end 44 can include a bone holding surface 46 having a curved surface 48 to assist in retaining the bone block 26 during resection of bone block 26 by shaping member 20, as will be discussed. While the bone holding surface 46 is shown as having the curved surface 48, it should be appreciated that the bone holding surface 46 can have any appropriate contour, such as flat, convex, concave, etc. to assist in orientating and retaining bone block 26 during resection.

The clamping system 16 can include a first clamping plate 50a and a second clamping plate 50b arranged to selectively engage support 14 and bone block 26 to orient and hold bone block 26 centrally in place on bone holding surface 46 during resection. The first plate 50a can be substantially identical to the second plate 50b, and thus the same reference numerals will be used to refer to features of both the first plate 50a and the second plate 50b. Both the first and second plates 50a, 50b can include a proximal end 52, a distal end 54, a support side 56 and an outer side 58 opposite the support side 56. The first and second plates 50a, 50b can each further include a pair of tabs or projections 60 disposed on support side 56, and a channel 62 extending from a front side 64 to a rear side 66 on outer side 58.

Figure 2:
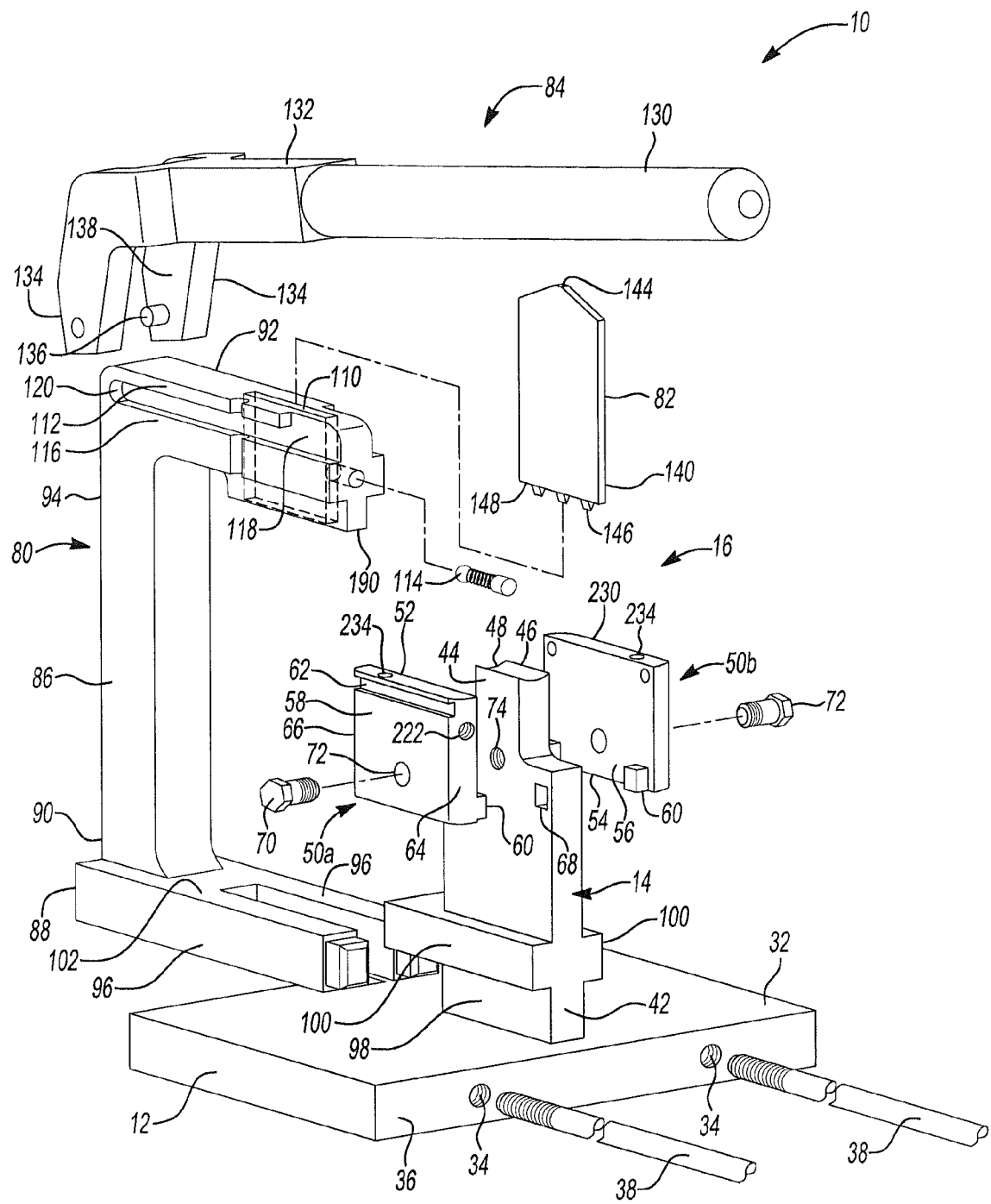
FIG. 2 is an exploded view of FIG. 1 according to the principles of the present disclosure.

Once bone block 26 has been positioned on the bone holding surface 46, the first and second clamping plates 50a, 50b can be positioned on support 14 such that the support side 56 can be contiguous to support 14 and projections 60 can be received in corresponding bores 68 that can be included in support 14. A pair of fasteners or bolts 70 can be received through an aperture 72 in the first and second plates 50a, 50b and threadably received in a corresponding bore 74 in support 14 to secure plates 50a, 50b to support 14 and retain bone block 26 as best shown in FIGS. 1 and 2. When clamping plates 50a, 50b are secured to support 14 as described above, a proximal portion of support side 56 can contact bone block 26 to assist in holding bone block 26 in place during resection of bone block 26. The plates 50a, 50b can form a first clamping structure that provides a first clamping force in a first direction perpendicular to support 14.

Second clamping system 18 can include a clamp support member 80, a clamping blade 82 and a lever arm 84. Clamp support member 80 can include a body member 86 having a first member 88 at a distal end 90 and a second member 92 at a proximal end 94, where each of the members can be integrally formed in a C-shaped structure as shown, for example, in FIGS. 1 and 2. While clamp support member 80 has been shown as an integrally formed C-shaped structure, it should be appreciated that clamp support member 80 can be formed from various structures that may not be integrally formed, such as three separately formed portions assembled together. First member 88 can serve as a base for clamp support member 80 and can include two longitudinally extending support members 96 spaced apart and arranged to be positioned adjacent to each side 98 of support 14 and on base surface 32. Support 14 can further include two longitudinally extending projections 100 protruding from sides 98 and arranged to engage a top surface 102 of support members 96 so as to retain clamp support member 80 in place during operation of second clamping system 18, as will be discussed.

Second member 92 of clamp support member 80 can extend substantially perpendicular to body member 86 and over support 14 as shown, for example, in FIG. 1. Second member 92 can include a captured through slot 110, a pair of longitudinally extending channels 112 and a biasing member 114 arranged to cooperate with slot 110. Slot 110 can be sized to slidably receive clamping blade 82 therethrough as shown, for example, in FIG. 1. The inner dimensions of slot 110 can be configured to substantially match corresponding outer dimensions of clamping blade 82 such that blade 82 can be received in sliding engagement with slot 110 with minimal clearance between blade 82 and slot 110.

Biasing member 114 can include any suitable biasing member, such as a conventional spring loaded ball plunger assembly 114 arranged to cooperate with slot 110 and engage clamping blade 82 when positioned in slot 110 as shown in FIG. 2. Ball plunger 114 can be arranged to maintain a vertical position of clamping blade 82 relative to second member 92 when blade 82 is not being acted upon by lever arm 84 or engaged with bone block 26, as will be discussed. The longitudinal extending channels 112 can be positioned on each side 116 of second member 92 as shown, for example, in FIGS. 2 and 3. Channels 112 can include an open end 118 and a captured end 120 at an opposite end.

Figure 3:
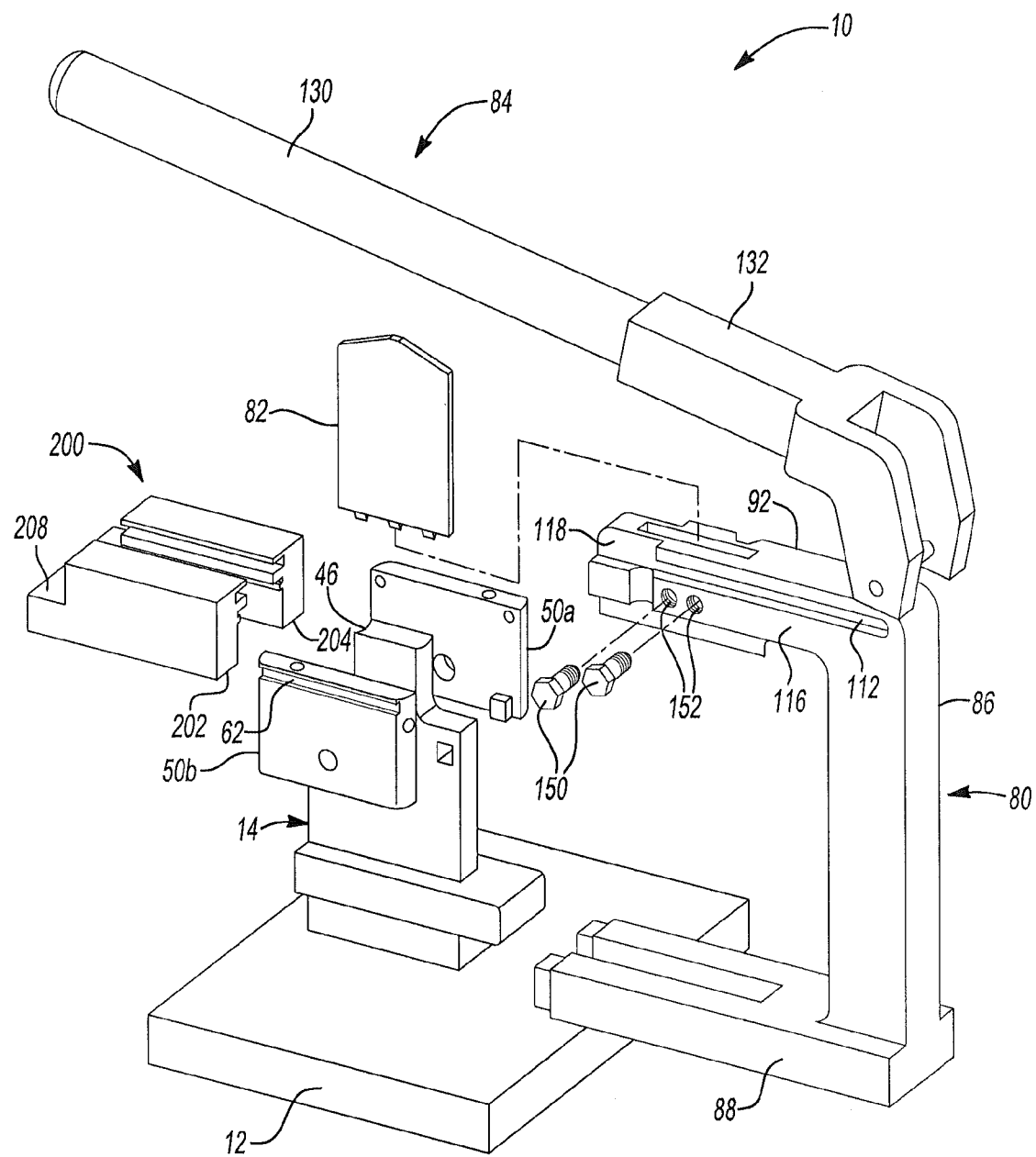
FIG. 3 is an exploded perspective view of the system for forming a tendon-bone graft according to the principles of the present disclosure.

The lever arm 84 can include a handle portion 130 and a body portion 132 that can include two extending members 134 spaced apart a distance from each other as shown, for example, in FIGS. 2 and 3. Lever arm 84 can be made from any suitable sterilizable material such as metal or a metal alloy. Extending members 134 can each include a pin 136 projecting from an inner face 138 of each extending member 134. The lever arm 84 can be engaged to second member 92 by sliding pins 136 into channel 112 through open end 118 until pins 136 are positioned at captured end 120.

Clamping blade 82 can include a substantially rectangular shape having a proximal end 140 and a distal end 144. The proximal end 140 can include at least one bone engagement member 146 protruding from a bottom surface 148. The bone engagement members 146 can include any suitable mechanism for engaging the bone block 26 to hold the bone block in place during resection, such as at least one spike, tooth, cleat, etc. The distal end 144 can extend beyond second member 92 when inserted through slot 110 and placed into contact with bone block 26 so as to enable a user to manipulate the clamping blade 82 by grasping the distal end 144, as well as enable the lever arm 84 to engage the clamping blade 82, as will be discussed. While clamping blade 82 is shown as having a rectangular shape, it should be appreciated that clamping blade 82 can be configured in other shapes suitable for insertion in slot 110 and engagement with bone block 26.

With the bone block 26 positioned on bone support surface 46 and captured by clamping plates 50a, 50b as shown in FIG. 1, clamping blade 82 can then be inserted through slot 110 and brought into a first engaged position contacting bone block 26. Lever arm 84 can then be brought into pivotal engagement with second member 92 as described above and pivoted about pins 136 so as to engage distal end 144 of clamping blade 82. A second clamping force perpendicular to the first clamping force can then be imparted on clamping blade 82 by lever arm 84 to clamp bone block 26 to bone support surface 46. The second clamping force can drive bone engagement members 146 into bone block 26 and clamping blade 82 to a second engaged position such that bottom surface 148 can contact bone block 26. It should be appreciated that bone engagement members 146 can be driven into bone block 26 to various points of engagement between the first and second engaged positions to clamp bone block 26 to support 14. With clamping blade 82 now engaging bone block 26, a pair of fasteners 150, such as set screws, can be threaded through apertures 152 in second member 92 to secure clamping blade 82 in the second engaged position as shown, for example, in FIGS. 3 and 4. Lever arm 84 can then optionally be removed from second member 92 by sliding pins 136 along channel 112 to open end 118 while still retaining the second clamping force.

Figure 4:
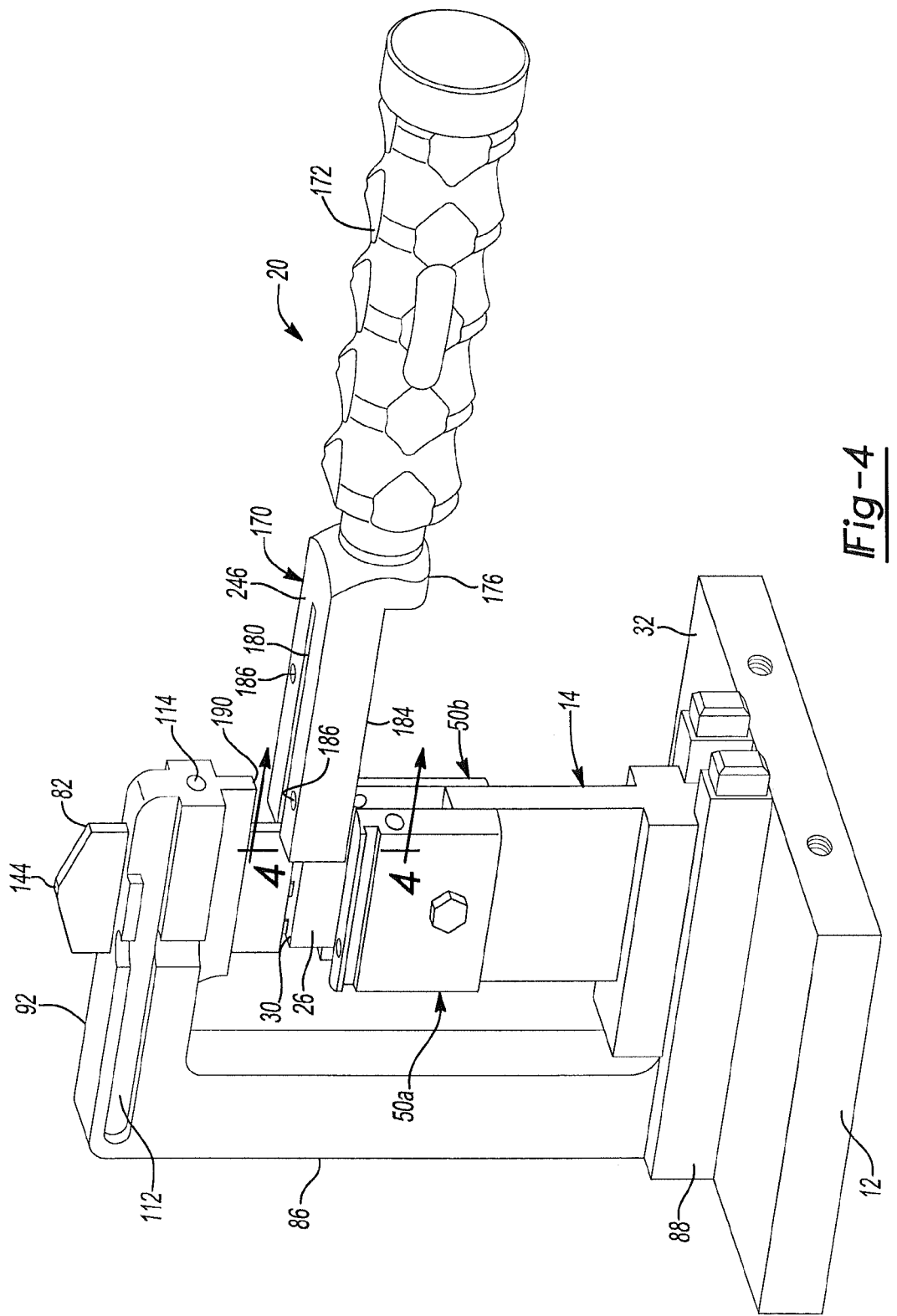
FIG. 4 is a perspective view of the system for forming a tendon-bone graft according to the principles of the present disclosure.
Figure 5:
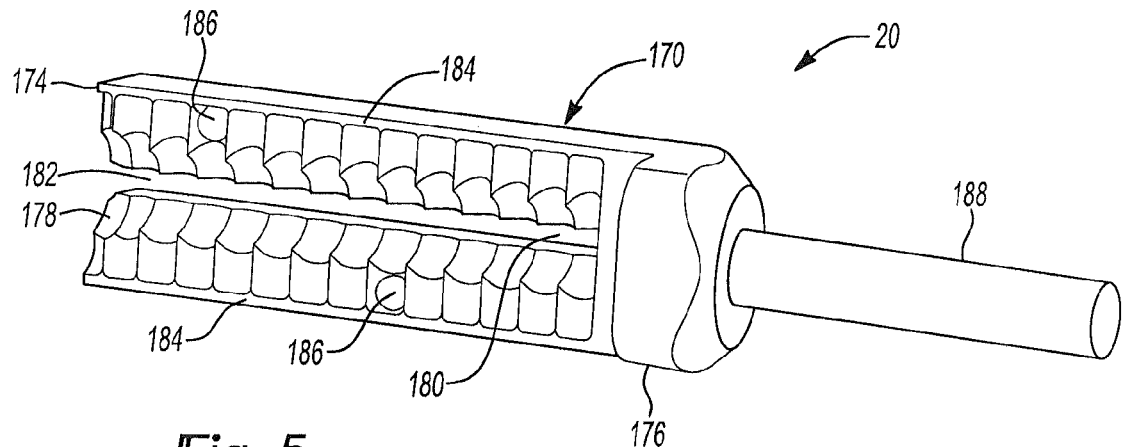
FIG. 5 is a perspective view of a shaping member of the system for forming a tendon-bone graft according to the principles of the present disclosure.

With reference to FIGS. 4 and 5, the shaping member 20 will be discussed in greater detail. Shaping member 20 can be operable to resect the bone block 26 and can include a body portion 170 and a handle portion 172. Body portion 170 can include a proximal end 174, a distal end 176, a plurality of teeth 178, and a longitudinally extending slot 180. The plurality of teeth 178 can extend from the proximal end 174 to the distal end 176 and can include an arcuate semi-circular shape separated by longitudinally extending slot 180 as shown, for example, in FIG. 5. Teeth 178 can have the same size from proximal end 174 to distal end 176, and can shape or resect bone block 26 when moving shaping member 20 in a first direction and a second opposite direction relative to bone block 26. Teeth 178 can extend outwardly from longitudinally extending slot 180 on bottom sliding surfaces 184 to permit the removal of any extraneous bone from bone block 26. Longitudinally extending slot 180 can include an open end 182 at proximal end 174 for receiving clamping blade 82 into slot 180 as will be discussed. Body portion 170 can further include an aperture 186 through each sliding surface 184 and a handle support member 188 extending from distal end 176.

Handle portion 172 can be made of any suitable sterilizable material such as plastic, metal or a metal alloy and can be affixed to handle support member 188 so as to abut distal end 176 as shown, for example, in FIG. 4. While handle portion 172 has been shown as being separately formed and affixed to body portion 170, it should be appreciated that handle portion can be integrally formed with body portion 170.

With the bone block 26 held in place by first and second plates 50a, 50b and clamping blade 82 and bone support surface 46 as described above, shaping member 20 can be advanced over clamping blade 82 such that slot 180 can receive clamping blade 82 in sliding engagement. Depending on the size of bone block 26, there may not be enough clearance between a top surface 30 of bone block 26 and a bottom surface 190 of second member 92 to receive shaping member 20 therebetween without resecting a portion of the top surface 30 prior to advancing shaping member 20 over clamping blade 82 (see FIG. 6). The extent to which a portion of the top surface 30 is resected also determines the amount of bone to be removed by shaping member 20, and preferably is chosen based on the depth of penetration of bone engagement members 146 to minimize such resected amount.

Figure 6:
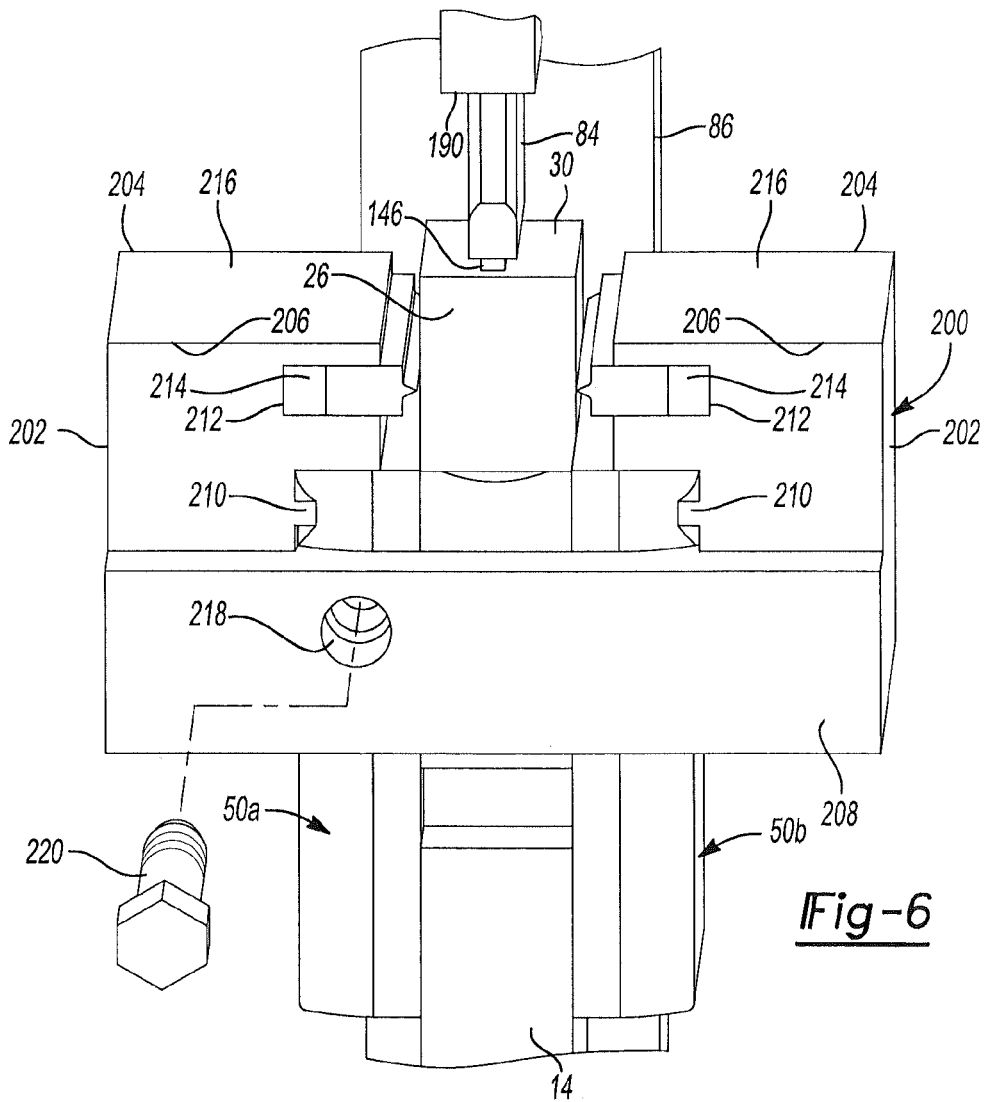
FIG. 6 is a partial front view of the system for forming a tendon-bone graft according to the principles of the present disclosure.
Figure 7:
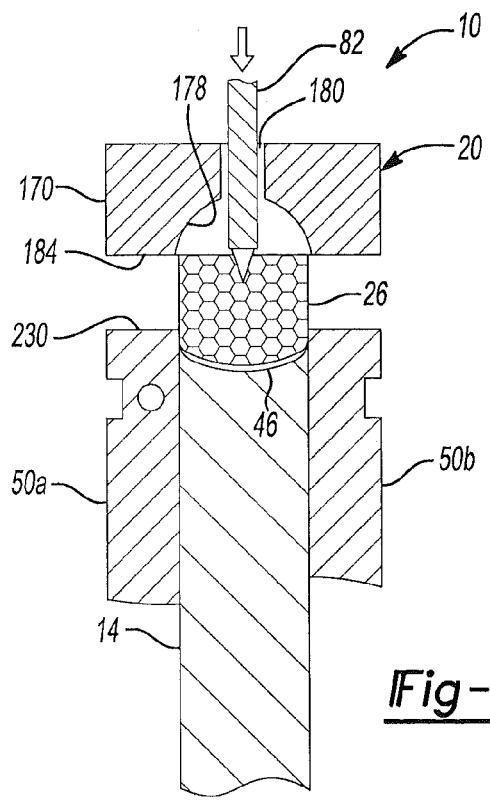
FIG. 7 is a simplified partial sectional view taken along line 4-4 of FIG. 4 illustrating a procedure for forming a tendon-bone graft using the system according to the principles of the present disclosure.

If the size of bone block 26 is such that resection can be required before advancing shaping member 20 over clamping blade 82, a guide 200 can be provided to facilitate shaping and resecting of the top surface 30 of bone block 26. With reference to FIGS. 3 and 6, guide 200 can include two side members 202 having proximal ends 204, distal ends 206, and a support member 208 connecting side members 202 at their distal ends 206 to form a general U-shape configuration as shown in FIG. 3. Side members 202 can include a longitudinally extending rib 210, and a channel 212 arranged to receive a wedge member 214. Guide 200 can be advanced over first and second plates 50a, 50b such that each rib 210 can engage the corresponding channel 62 in plates 50a, 50b to position guide 200 relative to bone block 26 as best shown in FIG. 6. Guide 200 can further include a top surface 216 and a threaded aperture 218 arranged to receive a fastener or bolt 220.

Once guide 200 is positioned on plates 50a, 50b, fastener 220 can be inserted through aperture 218 and threadably received in threaded bore 222 of first plate 50a to secure guide 200 in place. Wedge members 214 can be inserted into channels 212 of guide 200 and each engage a side of bone block 26 to hold bone block 26 in place during any resection of top surface 30. Wedge members 214 can generate a parallel clamping force to the first clamping force generated by plates 50a, 50b on bone block 26. Once guide 200 is secured, any portion of top surface 30 of bone block 26 that extends beyond top surface 216 can be resected using top surface 216 as a cutting guide. A reciprocating bone saw or other suitable cutting device can be used for the resection. Clamping blade 82 may need to be disengaged and raised from bone block 26 prior to resecting top surface 30 if bone engagement members 146 extend below top surface 216 of guide 200. Clamping blade 82 is re-engaged to bone block 26 and secured into the newly-resected top surface of bone block 26.

After mounting guide 200 and resecting top surface 30 as described above, wedge members 214 can be removed and then guide 200 can be removed from plates 50a, 50b after removing fastener 220. Shaping member 20 can then be advanced over clamping blade 82 such that slot 180 can receive clamping blade 82 in sliding engagement as generally shown in FIG. 4. Shaping member 20 can then be advanced in a first direction and a second opposite direction about clamping blade 82 in a direction perpendicular to the clamping force exerted by clamping blade 82 on bone block 26. For example, if clamping blade 82 is engaged with bone block 26 to clamp bone block 26 to bone holding surface 46, the clamp force can be generated generally vertically, parallel to support 14, and shaping member 20 can be advanced and retracted perpendicular to the clamp force, and thus, perpendicular to support 14 and clamping blade 82. Clamping blade 82 can also serve as a guide for advancing and retracting shaping member 20 to resect bone block 26.

Figure 8:
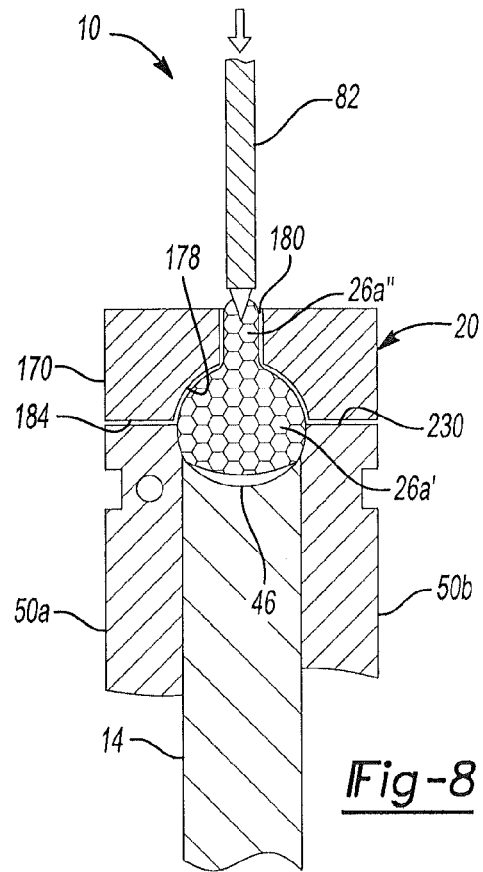
FIG. 8 is a simplified partial sectional view taken along line 4-4 of FIG. 4 illustrating a procedure for forming a tendon-bone graft using the system according to the principles of the present disclosure.

With additional reference to FIGS. 7-10, resection of bone block 26 will be discussed in greater detail. Advancing shaping member 20 over bone block 26 as described above can resect the bone block 26 shown in FIG. 7 to a partially cylindrical shape 26a' shown in FIG. 8. As shaping member 20 is advanced and retracted relative to bone block 26, a pressure can be exerted on shaping member 20 in the direction of the clamping force exerted by clamping blade 82 to assist in resecting bone block 26. Shaping member 20 can be advanced and retracted to resect bone block 26 until sliding surface 184 of shaping member 20 contacts a top surface 230 of first and second plates 50a, 50b thereby forming a partially cylindrical surface 26a' as shown in FIG. 8. A protruding surface 26a'' can remain due to slot 180 in shaping member 20 as also shown in FIG. 8.

Figure 9:
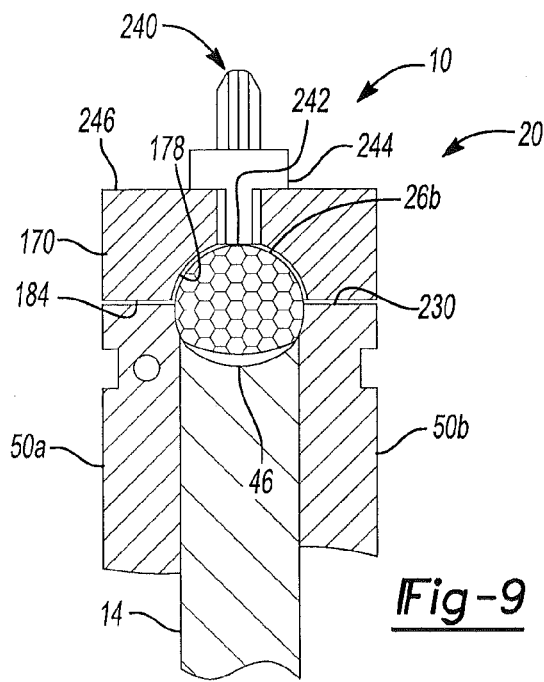
FIG. 9 is a simplified partial sectional view taken along line 4-4 of FIG. 4 illustrating a procedure for forming a tendon-bone graft using the system according to the principles of the present disclosure.
Figure 10:
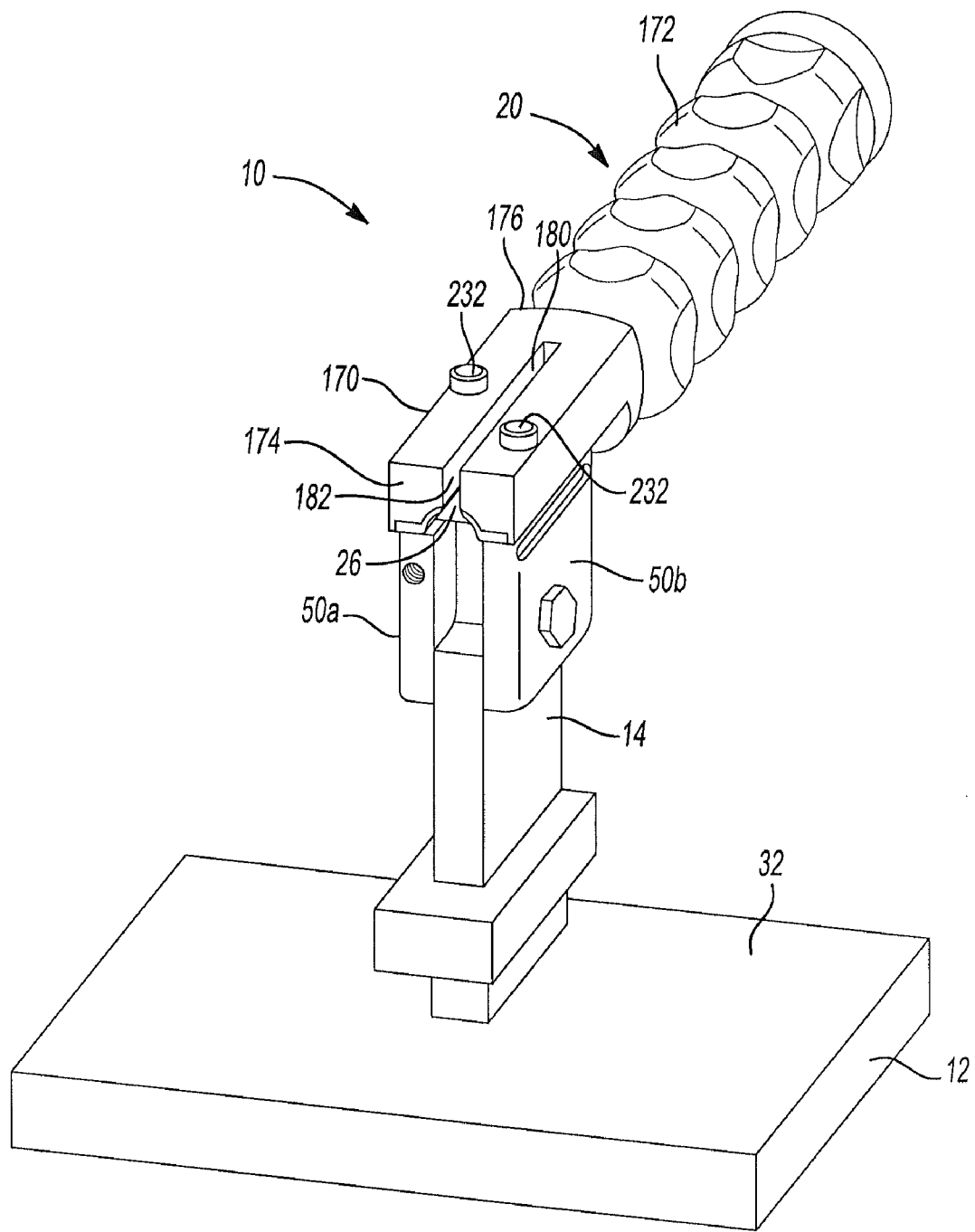
FIG. 10 is a partial view of the system for forming a tendon-bone graft according to the principles of the present disclosure.

The protruding surface 26a'' can be resected to form the substantially cylindrical shape 26b and to remove any indentations caused by engagement of the bone engagement members 146 with bone block 26, as shown in FIG. 9. In order to resect protruding surface 26a'', shaping member 20 can be secured to first and second plates 50a, 50b with fasteners 232 such that surfaces 184 of shaping member 20 engage top surfaces 230 of plates 50a, 50b. Fasteners 232 can be inserted through apertures 186 in shaping member 20 and can be threadably received in corresponding bores 234 of clamping plates 50a, 50b as generally shown in FIG. 10. Once shaping member 20 is secured, clamping blade 82 can be removed as well as lever arm 84, if not already removed. Clamp support member 80 can then be removed.

Once shaping member 20 is secured and clamping blade 82, lever arm 84, and clamp support member 80 are removed, protruding portion 26a'' can be resected with a cutting member 240 as shown in FIG. 9. Cutting member 240 can include a cutting surface 242, and a depth guide 244, and can include any suitable cutting member such as a carbide end mill. Cutting member 240 can be coupled to any appropriate tool to facilitate moving or rotating cutting member 240 to resect protruding surface 26a''. Cutting surface 242 can be arranged to contact and resect protrusion 26a'' until depth guide 244 contacts a top surface 246 of shaping member 20 to form the substantially cylindrical shape 26b, as shown in FIG. 9. It should be understood, however, that shaping member 20 and cutting member 240 may not necessarily be employed to resect protrusion 26a''. Rather, any suitable cutting member could be employed such as a broach with centralized cutting teeth, a bone saw, etc. It should also be understood that bone block 26 can be formed into alternative shapes in additional to the substantially cylindrical shape 26b, including but not limited to, substantially square or rectangular shapes, and the teeth 178 of shaping member 20 would conform to such alternative shapes.

Once protrusion 26a'' is resected, shaping member 20 and first and second plates 50a, 50b can be removed to release bone block 26 from support 14. Then, if desired, system 10 can be used to resect a second bone block 26 of a bone-tendon-bone graft. Otherwise, the prepared tendon-bone graft 24 can be inserted into a prepared anatomy (not shown) and bone graft forming system 10 can be optionally disassembled for sterilization.

With reference to FIGS. 11 and 12, a cutting guide 250 is shown. Guide 250 can be attached to the patella/patellar ligament/tibia portions 252 of donor tissue to recover the tendon-bone or bone-tendon-bone graft 24 that can be placed on support 14 as described above. Guide 250 can include a body portion 254 that can be handled by a user and a fixture portion 256 that can receive and guide a saw blade or suitable cutting device. Fixture portion 256 can be affixed to a ligament side of the donor tissue and secured in place with fasteners 258. Fasteners 258 can be any suitable fastener, such as a self tapping fastener, that can engage patella 260 to secure guide 250 to the patella. The fixture portion can include at least three cutting slots 262, 264, 266 spaced apart by at least two visualization areas 268. The cutting guide can be affixed to the donor tissue such that the slots 262-266 are oriented parallel to a direction of ligament 270. The cutting slots 262-266 can receive a cutting blade 272 to cut the patella/ligament into two tendon-bone grafts 24. While guide 250 is shown as having three cutting slots 262-266 that can form two tendon-bone grafts 24, it should be appreciated that cutting guide 250 can have a varying number of cutting clots, such as two slots to form one graft or four slots to form three grafts, depending on, for example, the size of the donor patella. The cutting slots can be positioned relative to each other such that a distance 274 between the slots corresponds to a predetermined dimension, such as a diameter, of the resected and formed bone block 26 with substantially cylindrical shape 26b.

While specific examples have been described in the specification and illustrated in the drawings, it will be understood by those of ordinary skill in the art that various changes can be made and equivalents can be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. A system for forming a bone graft, comprising:
   a support member that is adapted to support the bone graft;
   a first clamp that is adapted to engage the support member and the bone graft to orient and hold the bone graft to the support member in a first clamp direction;
   a second clamp that is adapted to engage the bone graft to clamp the bone graft to the support member in a second clamp direction, wherein the second clamp direction is different than the first clamp direction; and
   a shaping member that is operable to resect the bone graft; wherein the shaping member is moveable relative to at least one of the first clamp and the second clamp to resect the bone graft.

2. The system of claim 1, wherein the first clamp direction is perpendicular to the second clamp direction.

3. The system of claim 1, wherein the shaping member is moveable relative to the first or second clamp in a direction substantially perpendicular to a clamp force provided by the first or second clamp.

4. The system of claim 1, wherein the support member and the first and second clamps define at least four points of contact on the bone graft.

5. A system for forming a bone graft, comprising:
a support member that is adapted to support the bone graft, wherein the support member includes a bone engagement surface having a curved surface between a first side and a second side opposite the first side that is configured to mate with the bone graft;
a first clamp that is adapted to engage the support member and the bone graft to orient and hold the bone graft to the support member in a first direction;
a second clamp that is adapted to engage the bone graft to clamp the bone graft to the support member in a second clamp direction; and
a shaping member that is operable to resect the bone graft, wherein the shaping member is moveable relative to at least one of the first clamp and the second clamp to resect the bone graft.

6. A system for forming a bone graft, comprising:
a support member that is adapted to support the bone graft;
a first clamp that is adapted to engage the support member and the bone graft to orient and hold the bone graft to the support member in a first direction;
a second clamp that is adapted to engage the bone graft to clamp the bone graft to the support member in a second direction, wherein the second clamp includes a clamp guide and a clamp blade, the clamp guide having a first extending portion arranged to be coupled to the support member and a second extending portion extending over a bone engagement surface of the support member and defining a slot, the clamp blade arranged to be slidably received in the slot, the clamp blade including at least one bone engagement member at a proximal end that is adapted to engage a top surface of the bone graft to clamp the bone graft to the support member; and
a shaping member that is operable to resect the bone graft, wherein the shaping member is moveable relative to at least one of the first clamp and the second clamp to resect the bone graft; and
a base, wherein the support member includes a bone engagement surface on one end and is coupled to the base at an opposite end of the bone engagement surface.

7. The system of claim 6, wherein the support member further comprises at least one rib, and wherein the clamp guide first portion is slidably received between the rib and the base.

8. The system of claim 6, wherein the second portion further comprises a biasing member arranged to exert a biasing force on the clamp blade when the clamp blade is inserted into the slot so as to maintain a position of the clamp blade relative to the second portion in an absence of a force being exerted on the clamp blade to move the clamp blade relative to the second portion.

9. The system of claim 6, further comprising a lever arm arranged to be selectively pivotably coupled to the second portion of the clamp guide, wherein the lever arm is arranged to pivot about the second portion and engage a distal end of the clamp blade to exert a clamping force on the clamp blade and drive the at least one bone engagement member into the bone graft to an engaged position with a portion of the clamp blade remaining in the slot.

10. The system of claim 6, wherein the second portion of the clamp guide includes a first side and a second side opposite the first side, and a channel positioned in each of the first and second sides; and
wherein the system further comprises a lever arm having a pair of projections arranged to be slidably received in the channels to pivotably couple the lever arm to the second portion, the coupled lever arm arranged to pivot about the projections relative to the second portion and engage the clamp blade at a distal end to exert a clamping force on the clamp blade and drive the at least one bone engagement member into the bone graft to an engaged position with a portion of the clamp blade remaining in the slot.

11. The system of claim 10, wherein the second portion further comprises a locking member arranged to engage the second portion and the clamp blade to lock the clamp blade to the second portion when the clamp blade is received in the slot and in the engaged position.

12. The system of claim 6, wherein the first clamp comprises first and second clamp plates, the first clamp plate arranged to be coupled to the first side of the support member and engage the bone graft, and the second clamp plate arranged to be coupled to the second side of the support member and engage the bone graft to orient and hold the bone graft on the bone engaging surface.

13. The system of claim 12, further comprising a cutting table arranged to be secured relative to the bone graft to provide a guide surface for resecting any portion of the bone graft extending above the guide surface.

14. The system of claim 13, wherein the cutting table comprises:
a first side portion and a second side portion extending from a body portion and spaced apart from each other, the first and second side portions including a rib projecting towards a space between the side portions;
wherein the cutting table is arranged to be selectively slidably engaged with the clamp plates such that the ribs of the first and second side portions slidably engage respective channels positioned in the first and second clamp plates and the bone graft is received in the space between the side portions when the cutting table is engaged to the clamp plates; and
wherein the cutting table includes a channel in each side portion facing the space between the side portions, each channel arranged to receive a wedge member after the table top is engaged to the clamp plates, each wedge member arranged to engage one of the channels and a side of the bone graft thereby creating a clamping force parallel to a clamping force of the clamp plates.

15. The system of claim 6, wherein the shaping member comprises:
a body portion including a plurality of cutting teeth formed in a semi-circular shape and a through slot extending substantially along a longitudinal length of the body portion and bisecting the plurality of cutting teeth; and
a handle portion abutting the body portion;
wherein the shaping member is arranged to be advanced about the clamp blade such that the through slot receives the clamp blade in sliding engagement and the shaping member is moveable relative to the clamp blade to resect the bone graft with the plurality of teeth.

16. The system of claim 15, wherein the body portion further comprises a sliding surface positioned on each side of the longitudinally extending slot, and wherein the plurality of cutting teeth can further extend outwardly from the longitudinally extending slot on the sliding surfaces.

17. The system of claim 15, wherein the shaping member is moveable relative to the clamp blade in a first direction and a second direction opposite the first direction to resect the bone graft a predetermined amount with the body portion arranged to engage a top surface of the clamp plates when the bone graft has been resected by the predetermined amount.

18. The system of claim 15, wherein the shaping member further comprises an aperture positioned on each side of the slot and arranged to receive a fastener for selectively securing the shaping member to a top surface of the first and second clamp plates after resecting the bone graft with the plurality of teeth.

19. The system of claim 18, wherein the shaping member body portion further comprises a top surface on an opposite side of the plurality of teeth, and wherein the top surface is adapted to receive a cutting blade in the through slot, the cutting blade being arranged to resect the bone graft, the cutting blade including a projection arranged to engage the top surface of the body portion to limit a depth the cutting blade can resect the bone graft relative to the top surface.

20. The system of claim 6, further comprising at least one elongated base extension, the base extension arranged to be selectively received in a threaded bore of the base.

21. A system for forming a bone graft, comprising:
a support member that is adapted to support the bone graft;
a first clamp that is adapted to engage the support member and the bone graft to orient and hold the bone graft to the support member in a first direction;
a second clamp that is adapted to engage the bone graft to clamp the bone graft to the support member in a second direction; and
a shaping member that is operable to resect the bone graft, wherein the shaping member is moveable relative to at least one of the first clamp and the second clamp to resect the bone graft, wherein the bone graft includes a tendon-bone graft, and wherein the system further comprises a cutting fixture arranged to be affixed to a tendon-bone portion of donor tissue to provide a guide for cutting the donor tendon-bone portion into the tendon-bone graft that is adapted to be supported by the support member, the cutting fixture comprising:
a fixture portion having at least two cutting slots spaced apart a predetermined distance, the cutting slots arranged to be positioned parallel to a tendon of the donor tendon-bone portion upon securing the cutting fixture to the donor tendon-bone portion, the cutting slots adapted to receive a cutting blade to cut the donor tendon-bone portion into the tendon-bone graft; and
at least one fastener arranged to engage a bone of the donor tendon-bone portion to secure the cutting fixture to the donor tendon-bone portion.

22. The system of claim 21, wherein the at least two cutting slots comprises three cutting slots including a center slot and a side slot positioned on each side of the center slot, the side slots spaced apart the predetermined distance from the center slot such that each of the three cutting slots is adapted to receive the cutting blade to cut the tendon-bone portion into two tendon-bone grafts.

23. A system for forming a bone graft, comprising:
a base member;
a support member coupled to the base member at a distal end and adapted to support the bone graft at a proximal end, the support member including a first side, a second side opposite the first side, and a bone engagement surface at the proximal end configured to mate with the bone graft;
a side clamp having first and second clamp plates adapted to engage the bone graft and respective first and second sides of the support member to orient and hold the bone graft on the support member, the first and second clamp plates each including an aperture for receiving a fastener to secure the clamp plates to the support member and the bone graft;
a second clamp that is adapted to engage a top surface of the bone graft to clamp the bone graft to the support member, the second clamp including body portion having a first extending portion at a distal end coupled to the support member and a second extending portion at a proximal end having a pair of channels and defining a through slot, the second portion extending over the bone engagement surface, the through slot arranged to receive a clamp blade in sliding engagement with the through slot, the clamp blade having a distal end and a proximal end with at least one bone engagement member;
a lever arm, the lever arm having a pair of projections arranged to be slidably received in the channels of the second extending portion so as to pivotably couple the lever arm to the second extending portion, the coupled lever arm arranged to be pivoted about the projections so as to engage the distal end of the clamp blade and drive the at least one bone engagement member into the top surface of the bone graft to clamp the bone graft to the support member; and
a shaping member that is moveable relative to the clamp blade to resect the bone graft, the shaping member including a body portion having a through slot and plurality of cutting teeth on one side, the plurality of cutting teeth having an arcuate semi-circular shape and extending outwardly from the through slot on a bottom sliding surface positioned on each side of the through slot, the through slot having an open end and extending substantially along a longitudinal length of the body portion, the shaping member adapted to be moved about the clamp blade such that the clamp blade is received in the shaping member through slot and guides the shaping member as the shaping member is moved relative to the clamp blade to resect the bone graft.

24. The system of claim 23, further comprising:
a cutting table arranged to provide a guide surface for resecting the bone graft, the cutting table including first and second side portions extending from a body portion and spaced apart from each other, the first and second side portions including a rib projecting towards a space between the side portions;
wherein the cutting table is further arranged to be selectively slidably engaged with the clamp plates such that the ribs of the first and second side portions engage a corresponding channel in an outer side of each of the first and second clamp plates, and wherein the bone graft is received in the space between the first and second side portions when the cutting table is engaged to the clamp plates.

* * * * *